US00PP21327P2

(12) United States Plant Patent
Bernuetz

(10) Patent No.: US PP21,327 P2
(45) Date of Patent: Sep. 28, 2010

(54) ***EUPHORBIA* PLANT NAMED 'BONPRILIPCOM'**

(50) Latin Name: ***Euphorbia pulcherrima* Willd. ex *Klotzsch×Euphorbia cornastra***
Varietal Denomination: Bonprilipcom

(75) Inventor: Andrew Bernuetz, Silverdale (AU)

(73) Assignee: Bonza Botanicals Pty. Ltd., Yellow Rock, NSW (AU)

( * ) Notice: Subject to any disclaimer, the term of this patent is extended or adjusted under 35 U.S.C. 154(b) by 0 days.

(21) Appl. No.: 12/387,559

(22) Filed: May 4, 2009

(51) Int. Cl.
*A01H 5/00* (2006.01)

(52) U.S. Cl. ..... Plt./302

(58) Field of Classification Search ..... Plt./302, Plt./303, 304, 305, 306, 307
See application file for complete search history.

(56) References Cited

OTHER PUBLICATIONS

GTITM UPOVROM Citation for 'Bonprilipcom' as per QZ PBR 20090533; Mar. 23, 2009.*

* cited by examiner

*Primary Examiner*—Kent L Bell

(74) *Attorney, Agent, or Firm*—C. A. Whealy

(57) ABSTRACT

A new and distinct cultivar of *Euphorbia* plant named 'Bonprilipcom' characterized by its compact and mounded plant habit; moderately vigorous growth habit; freely branching habit; strong stems that resist breakage; dark green-colored leaves; inflorescences with pink-colored flower bracts; good post-production longevity; and relative tolerance to low production temperatures.

1 Drawing Sheet

Botanical designation: *Euphorbia pulcherrima* Willd. ex *Klotzsch×Euphorbia cornastra.*

Cultivar denomination: 'BONPRILIPCOM'.

CROSS-REFERENCED TO RELATED APPLICATIONS:

Title: *Euphorbia* Plant Named 'Bonpridepcom'
Applicant: Andrew Bernuetz
Filed: U.S. Plant patent application Ser. No. 12/387,564.
Title: *Euphorbia* Plant Named 'Bonpripapcom'
Applicant: Andrew Bernuetz
Filed: U.S. Plant Patent application Ser. No. 12/387,561.

BACKGROUND OF THE INVENTION

The present invention relates to a new and distinct cultivar of *Euphorbia* plant, an interspecific hybrid botanically known as *Euphorbia pulcherrima* Willd. ex *Klotzsch×Euphorbia cornastra,* and hereinafter referred to by the name 'Bonprilipcom'.

The new *Euphorbia* plant is a naturally-occurring whole plant mutation of *Euphorbia pulcherrima* Willd. ex *Klotzsch×Euphorbia cornastra* 'Bonpripicom', disclosed in U.S. Plant patent application Ser. No. 12/387,562. The new *Euphorbia* was discovered and selected by the Inventor as a single plant from within a population of plants of 'Bonpripicom' in a controlled greenhouse environment in Yellow Rock, New South Wales, Australia in January, 2005.

Asexual reproduction of the new *Euphorbia* plant by terminal vegetative cuttings in a controlled greenhouse environment in Yellow Rock, New South Wales, Australia since February, 2005, has shown that the unique features of this new

*Euphorbia* plant are stable and reproduced true to type in successive generations of asexual reproduction.

SUMMARY OF THE INVENTION

Plants of the new *Euphorbia* have not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Bonprilipcom'. These characteristics in combination distinguish 'Bonprilipcom' as a new and distinct cultivar of *Euphorbia:*

1. Compact and mounded plant habit.
2. Moderately vigorous growth habit.
3. Freely branching habit.
4. Strong stems that resist breakage.
5. Dark green-colored leaves.
6. Inflorescences with pink-colored flower bracts.
7. Good post-production longevity.
8. Relatively tolerant to low production temperatures.

In side-by-side comparisons conducted in Higashiomi, Shiga, Japan, plants of the new *Euphorbia* differed from plants of the parent, 'Bonpripicom', primarily in flower bract color as plants of 'Bonpripicom' have darker-colored flower bracts.

Plants of the new *Euphorbia* can be compared to plants of *Euphorbia pulcherrima* Willd. ex *Klotzsch×Euphorbia cornastra* 'Bonpridepcom', disclosed in U.S. Plant patent application Ser. No. 12/387,564. Plants of the new *Euphorbia* differ from plants of 'Bonpridepcom' primarily in flower bract color as plants of 'Bonpridepcom' have red purple-colored flower bracts.

Plants of the new *Euphorbia* can be compared to plants of *Euphorbia pulcherrima* Willd. ex *Klotzsch*×*Euphorbia cornastra* 'Bonpripapcom', disclosed in a U.S. Plant patent application Ser. No. 12/387,561. Plants of the new *Euphorbia* differ from plants of 'Bonpripapcom' primarily in flower bract color as plants of 'Bonpripapcom' have light pink-colored flower bracts.

Plants of the new *Euphorbia* can also be compared to plants of the *Euphorbia pulcherrima* Willd. ex *Klotzsch*×*Euphorbia cornastra* 'Eckcory', disclosed in U.S. Plant Pat. No. 15,849. In side-by-side comparisons conducted in Higashiomi, Shiga, Japan, plants of the new *Euphorbia* differed from plants of 'Eckcory' in the following characteristics:

1. Plants of the new *Euphorbia* were more compact and had shorter internodes than plants of 'Eckcory'.
2. Plants of the new *Euphorbia* had broader leaves than plants of 'Eckcory'.
3. Inflorescences of plants of the new *Euphorbia* had more flower bracts than inflorescences of plants of 'Eckcory'.
4. Inflorescences of plants of the new *Euphorbia* had longer and broader flower bracts than inflorescences of plants of 'Eckcory'.
5. Inflorescences of plants of the new *Euphorbia* had lighter-colored flower bracts than inflorescences of plants of 'Eckcory'.
6. Inflorescences of plants of the new *Euphorbia* had more cyathia than inflorescences of plants of 'Eckcory'.

BRIEF DESCRIPTION OF THE PHOTOGRAPHS

The accompanying photographs illustrate the overall appearance of the new *Euphorbia*. These photographs show the colors as true as it is reasonably possible to obtain in colored reproductions of this type. Colors in the photographs may differ slightly from the color values cited in the detailed botanical description which accurately describe the colors of the new *Euphorbia* plant.

The photograph at the top of the sheet comprises a side perspective view of a typical flowering plant of 'Bonprilipcom' grown in a container.

The photograph at the bottom of the sheet is a close-up view of a typical inflorescence of 'Bonprilipcom'.

DETAILED BOTANICAL DESCRIPTION

Plants used in the aforementioned photographs and the following observations and measurements describe plants grown in containers in Higashiomi, Shiga, Japan during the autumn in a polyethylene-covered greenhouse and under conditions and practices which approximate those generally used in commercial *Euphorbia* production. During the production of the plants, day temperatures averaged 23° C. and night temperatures averaged 13° C. Measurements and numerical values represent averages for typical flowering plants. Plants were four months old when the photographs and the description were taken. In the following description, color references are made to The Royal Horticultural Society Colour Chart, Fourth Edition, 2001, except where general terms of ordinary dictionary significance are used.

Botanical classification: *Euphorbia pulcherrima* Willd. ex *Klotzsch*×*Euphorbia cornastra* 'Bonprilipcom'.

Parentage: Naturally-occurring whole plant mutation of the *Euphorbia pulcherrima* Willd. ex *Klotzsch*×*Euphorbia cornastra* 'Bonpripicom', disclosed in U.S. Plant patent application Ser. No. 12/387,562.

Propagation:

*Type.*—Terminal vegetative cuttings.

*Time to initiate roots, summer.*—About one week at 20° C. to 25° C.

*Time to initiate roots, winter.*—About two weeks at 15° C. to 20° C.

*Time to produce a rooted young plant, summer.*—About three weeks at 20° C. to 25° C.

*Time to produce a rooted young plant, winter.*—About four weeks at 15° C. to 20° C.

*Root description.*—Fibrous; white in color.

*Rooting habit.*—Freely branching; moderately dense.

Plant description:

*Plant habit and form.*—Compact and mounded plant habit; inverted triangle; inflorescences positioned above the foliar plane; moderately vigorous growth habit.

*Plant height.*—About 16.6 cm.

*Plant diameter or spread.*—About 20.6 cm.

*Lateral branch description.*—Quantity: Freely branching habit, about four lateral branches develop per plant; pinching is typically not required. Length: About 9 cm. Diameter: About 2.8 mm. Internode length: About 7 mm. Strength: Strong. Texture: Smooth, glabrous. Color: Close to 146B.

*Foliage description.*—Arrangement: Alternate, simple. Length: About 10 cm. Width: About 5.5 cm. Shape: Ovate. Apex: Acute. Base: Truncate. Margin: Entire; slightly undulate. Venation pattern: Pinnate, reticulate. Texture, upper and lower surfaces: Smooth, glabrous. Color: Developing leaves, upper surface: Close to 141B tinted with close to between 56D and 62B. Developing leaves, lower surface: Close to 138B tinted with close to 56D. Fully expanded leaves, upper surface: Close to 137A to 137B; venation, close to 145C. Fully expanded leaves, lower surface: Close to 137A to 137B; venation, close to 145C. Petiole: Length: About 2.7 cm. Diameter: About 1.9 mm. Texture, upper and lower surfaces: Smooth, glabrous. Color, upper surface: Close to 145B tinted with close to 200C. Color, lower surface: Close to 145B.

Inflorescence description:

*Inflorescence type and habit.*—Inflorescences are compound corymbs of cyathia with colored flower bracts subtending the cyathia; inflorescences positioned above the foliage.

*Quantity of inflorescence.*—One inflorescence develops per lateral branch.

*Fragrance.*—Not detected.

*Natural flowering season.*—Plants typically flower during the autumn and winter in Higashiomi, Shiga, Japan; inflorescence initiation and development can also be induced under artificial long nyctoperiod/short photoperiod conditions. Early flowering habit, plants flower about 50 days under natural season conditions in Higashiomi, Shiga, Japan.

*Post-production longevity.*—Good post-production longevity; plants of the new *Euphorbia* maintain good substance and bract color for about seven weeks.

*Flower bracts.*—Quantity per inflorescence: About 19. Length, largest bracts: About 7.6 cm. Width, largest bracts: About 4.2 cm. Shape: Narrowly ovate. Apex: Acute. Base: Truncate. Margin: Entire. Texture, upper and lower surfaces: Smooth, glabrous. Aspect: Close to perpendicular to the stem axis. Venation pattern:

Pinnate, reticulate. Color: Developing or transitional bracts, upper surface: Between N57B and 62A; towards the margins, close to 62D. Developing or transitional bracts, lower surface: Close to 65D. Fully expanded bracts, upper surface: Close to 62C; towards the margins, close to 62D; venation, close to 186A. Fully expanded bracts, lower surface: Close to 65D; venation, close to 145A to 145C. Flower bract petiole: Length: About 1.5 cm. Diameter: About 1.6 mm. Texture, upper and lower surfaces: Smooth, glabrous. Color, upper and lower surfaces: Close to 145B.

*Cyathia.*—Quantity per corymb: About 16. Diameter of cyathia cluster: About 2.2 cm. Length, individual cyathium: About 6.1 mm. Width, individual cyathium: About 5.6 mm. Shape, individual cyathium: Globose. Color: Close to 146B. Nectaries: Quantity per cyathium: One or two. Size: About 4 mm by 2 mm. Color: Close to 151B.

*Peduncles.*—Length: About 2 mm. Diameter: About 1 mm. Strength: Strong. Aspect: Mostly upright. Texture: Smooth, glabrous. Color: Close to 145B.

*Reproductive organs.*—Stamens: Quantity per cyathium: Few. Anther shape: Lanceolate or globose. Anther length: About 1 mm to 10 mm. Anther color: Close to 187B. Amount of pollen: Scarce. Pistils: Plants of the new *Euphorbia* do not develop pistils.

*Seed/fruit.*—Seed and fruit production has not been observed.

Disese/pest resistance: Plants of the new *Euphorbia* have not been shown to be resistant to pathogens and pests common to *Euphorbias.*

Temperature tolerance: Plants of the new *Euphorbia* have been observed to tolerate temperatures ranging from about 8° C. to about 40° C.

It is claimed:

1. A new and distinct *Euphorbia* plant named 'Bonprilipcom' as illustrated and described.

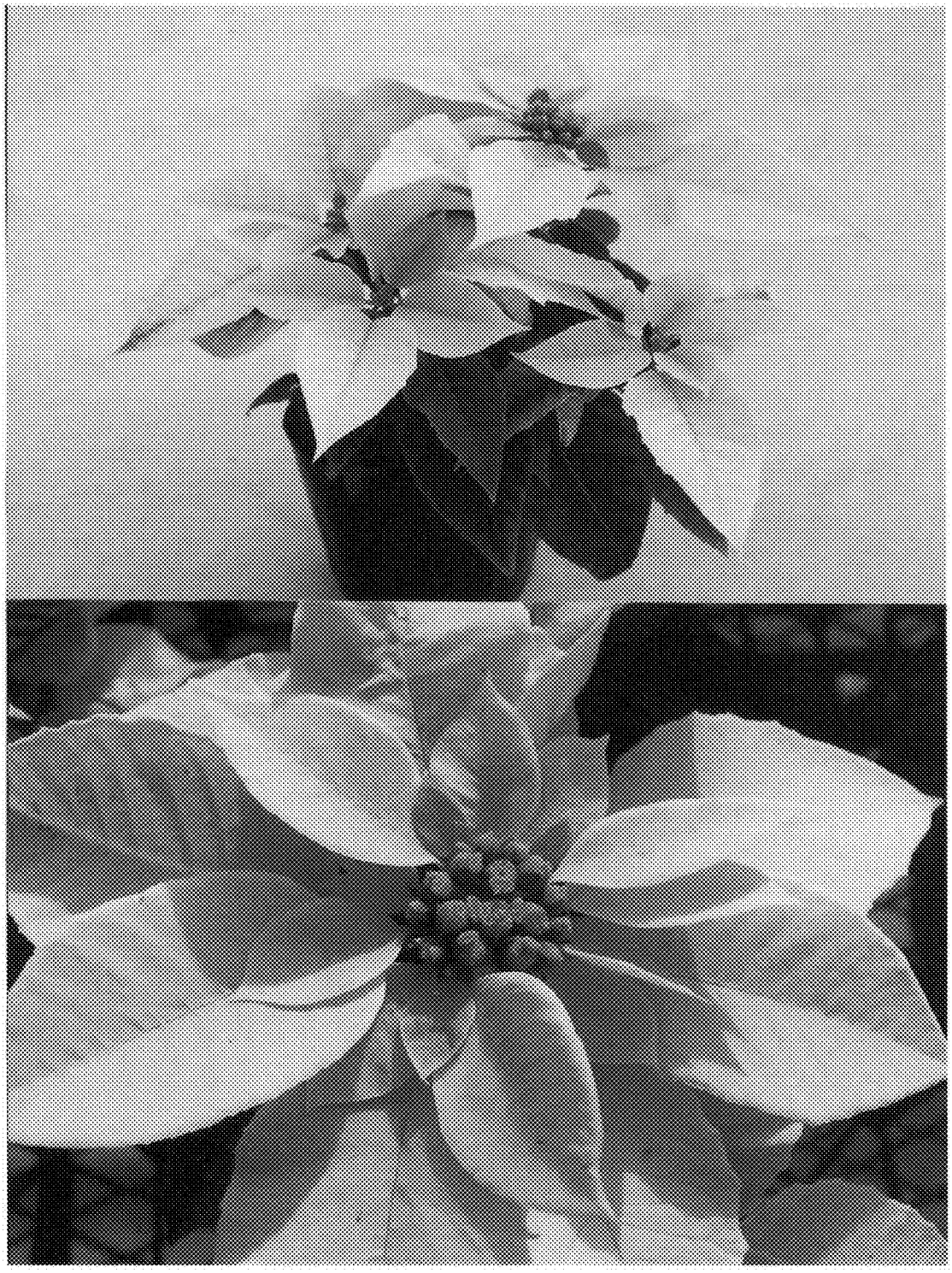

* * * * *